United States Patent
Focht et al.

(10) Patent No.: US 8,235,995 B2
(45) Date of Patent: Aug. 7, 2012

(54) BONE STAPLE WITH COMPRESSIBLE DEFORMATION REGION

(75) Inventors: Louse M. Focht, Del Mar, CA (US);
Rebecca H. Wahl, Escondido, CA (US);
John C. Nadworny, La Jolla, CA (US);
Stephen A. Maguire, Shelton, CT (US);
Ernie Corrao, Bethel, CT (US); Robert H. Humphries, Jr., Danbury, CT (US)

(73) Assignee: Tornier, Inc., Edina, MN (US)

( * ) Notice: Subject to any disclaimer, the term of this patent is extended or adjusted under 35 U.S.C. 154(b) by 1447 days.

(21) Appl. No.: 11/820,604

(22) Filed: Jun. 19, 2007

(65) Prior Publication Data

US 2008/0319443 A1    Dec. 25, 2008

(51) Int. Cl.
*A61B 17/84* (2006.01)
*A61F 2/30* (2006.01)

(52) U.S. Cl. .......................................................... 606/75
(58) Field of Classification Search ................ 606/75, 606/219, 220, 221
See application file for complete search history.

(56) References Cited

U.S. PATENT DOCUMENTS

| | | | | |
|---|---|---|---|---|
| 2,910,067 | A | * | 10/1959 | White .............................. 606/221 |
| 4,456,006 | A | * | 6/1984 | Wevers et al. .................... 606/75 |
| 5,352,229 | A | * | 10/1994 | Goble et al. ...................... 606/75 |
| 5,779,707 | A | * | 7/1998 | Bertholet et al. ................. 606/75 |
| 5,947,999 | A | * | 9/1999 | Groiso ............................. 606/219 |

OTHER PUBLICATIONS

Advancing the Science of Foot and Ankle Surgery Brochure. The Applicants admit that this brochure is prior art, 2005.

* cited by examiner

*Primary Examiner* — Anu Ramana
(74) *Attorney, Agent, or Firm* — Faegre Baker Daniels LLP

(57) ABSTRACT

A bone staple (10) for securing a first bone region (12A) to a second bone region (12B) includes a staple body (16) having a first leg section (18), a second leg section (20), and a connector section (22). The first leg section (18) is insertable into the first bone region (12A). The second leg section (20) is insertable into the second bone region (12B). The connector section (22) connects the first leg section (18) to the second leg section (20). The connector section (22) includes a deformable region (22A) that is movable from a first configuration (14A) in which the leg sections (18) (20) are spaced apart a first distance (24) and a second configuration (14B) in which the leg sections (18) (20) are spaced apart a second distance (26) that is less than the first distance (24). In one embodiment, compression of the deformable region (22A) causes the deformable region (22A) to move from the first configuration (14A) to the second configuration (14B). As a result of this design, the bone staple (10) can easily be moved from the first configuration (14A) to the second configuration (14B). The deformable region (22A) can be substantially square ring shaped and can define a region aperture (22D) that is substantially square in the first configuration (14A). Further, the deformable region (22A) can be substantially oval ring shaped and the region aperture (22D) can be generally rectangular shaped in the second configuration (14B).

16 Claims, 6 Drawing Sheets

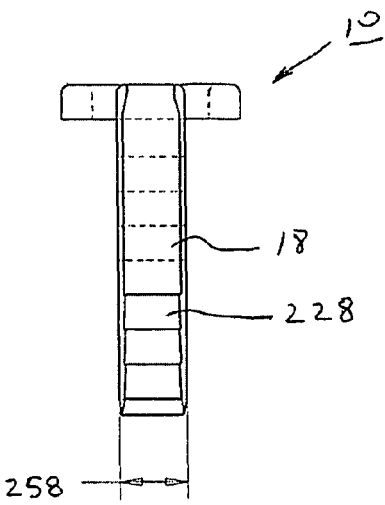
FIG. 2C
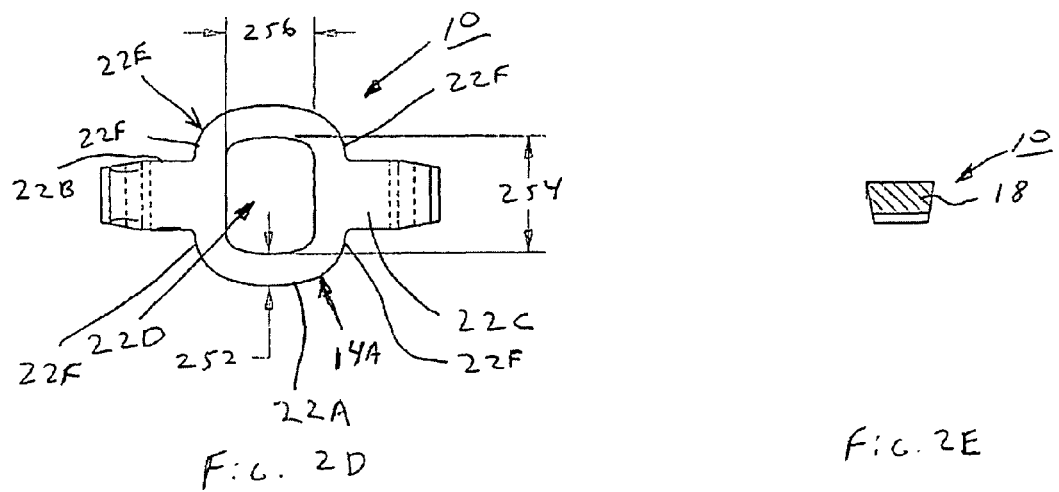
FIG. 2D
FIG. 2E

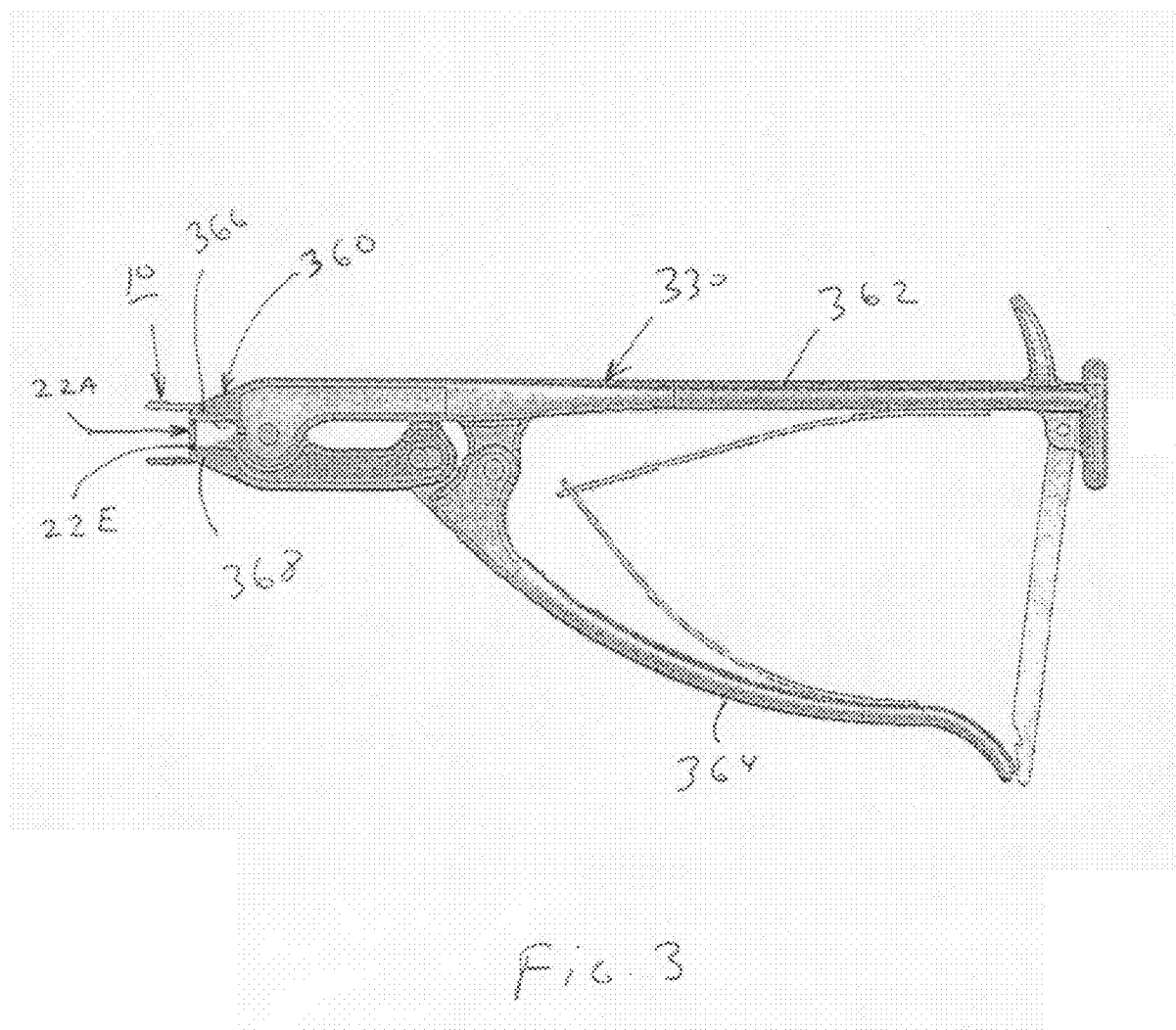

BONE STAPLE WITH COMPRESSIBLE DEFORMATION REGION

BACKGROUND

It is often necessary to fuse two bone regions to repair a fracture or to fuse a joint. On type of device used to fuse two bone regions is a compression staple that is generally "U" shaped and includes a pair of spaced apart leg sections and a connector section that connects the leg sections together. In one type of compression staple, the connector section includes a somewhat open diamond shaped region. In this type of device, the leg sections are insertable into apertures in bone regions. Subsequently, the diamond shaped region is expanded with an expansion tool. The expansion of the diamond shaped region causes the leg sections to move towards each other. This pulls the bone regions together.

Unfortunately, with this design compression staple can have a relatively large lateral profile when the staple is fully expanded.

SUMMARY

The present invention is directed toward a bone staple for securing a first bone region to a second bone region. The bone staple includes a staple body having a first leg section, a second leg section, and a connector section. The first leg section is insertable into the first bone region. The second leg section is insertable into the second bone region. The connector section connects the first leg section to the second leg section. The connector section includes a deformable region that is movable from a first configuration in which the leg sections are spaced apart a first distance and a second configuration in which the leg sections are spaced apart a second distance that is less than the first distance. In one embodiment, compression of the deformable region causes the deformable region to move from the first configuration to the second configuration. As a result of this design, the bone staple can easily be moved from the first configuration to the second configuration.

In one embodiment, the deformable region is substantially square ring shaped and defines a region aperture that is substantially square in the first configuration. Further, in one embodiment, the deformable region is substantially oval ring shaped and the region aperture is generally rectangular shaped in the second configuration.

Additionally, the connector section can include a first non-deformable region and a spaced apart second non-deformable region. Moreover, the staple body can include a pair of spaced apart first leg sections that extend into the first bone region and a pair of spaced apart second leg sections that extend into the second bone region.

The present invention is also directed to a method for securing a first bone region to a second bone region. The method can include the steps of (i) providing providing the staple body, (ii) inserting the first leg section into the first bone region; (iii) inserting the second leg section into the second bone region; and (iv) compressing the deformable region to move the deformable region from the first configuration to the second configuration.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2C is an end view of the bone staple of FIG. 2A;

FIG. 2D is a top view of the bone staple of FIG. 2A;

FIG. 2E is a cut-away view taken on line 2E-2E in FIG. 2A;

FIG. 3 is a side view of a compression tool and the bone staple of FIG. 1;

DESCRIPTION

Figure 1A:
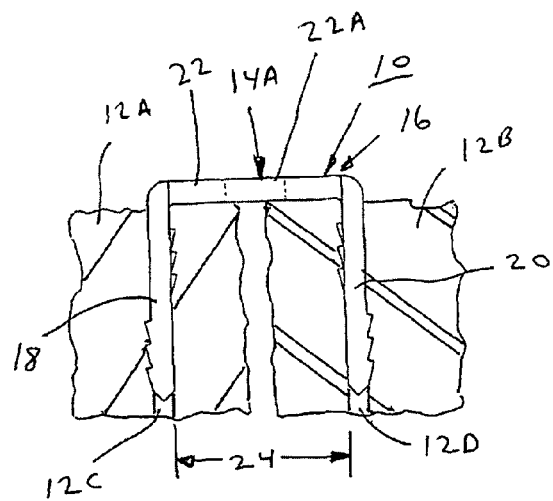
FIG. 1A is a simplified side view, in partial cut-away of a first bone region, a second bone region, and a bone staple having features of the present invention in a first configuration.
Figure 1B:
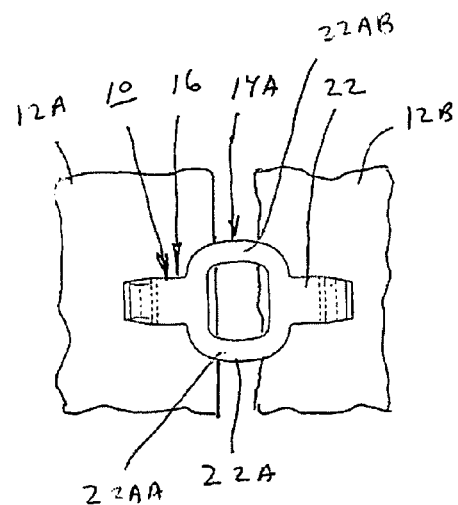
FIG. 1B is a simplified top view of the first bone region, the second bone region, and the bone staple of FIG. 1A in the first configuration.
Figure 1C:
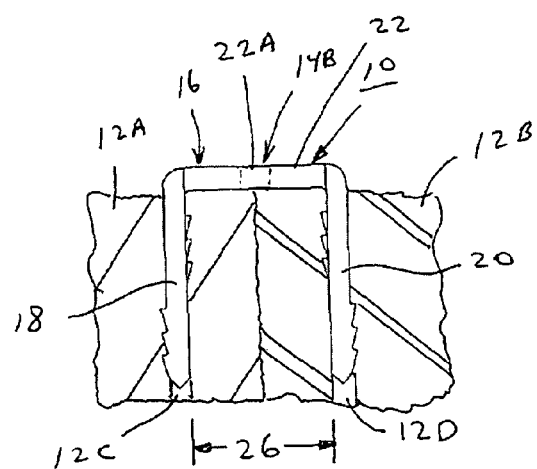
FIG. 1C is a simplified side view, in partial cut-away, of the first bone region, the second bone region, and the bone staple of FIG. 1A in a second configuration.

FIGS. 1A-1D are alternative, simplified illustrations of a portion of a bone staple 10 having features of the present invention, a first bone region 12A and a second bone region 12B of a human. In FIGS. 1A and 1B, the bone staple 10 is in a first configuration 14A and the bone regions 12A, 12B are separated; and in FIGS. 1C and 1D, the bone staple 10 is in a second configuration 14B and the bone regions 12A, 12B are adjacent to each other. In this embodiment, the bone staple 10 is used to urge and retain the bone regions 12A, 12B together so that the bone regions 12A, 12B are fused together. The type and location of the bone regions 12A, 12B urged together can vary. For example, the bone staple 10 can be used to fuse a fracture of a human bone, to immobilize and fuse a human joint, or to fuse together adjacent bones.

In this embodiment, the bone staple 10 includes a generally inverted "U" shaped staple body 16 having a first leg section 18, a second leg section 20 and a connector section 22. The first leg section 18 is insertable into a first bone aperture 12C in the first bone region 12A. The second leg section 20 is insertable into a second bone aperture 12D in the second bone region 12D. Alternatively, the leg sections 18, 20 can be inserted into the respective bone region 12A, 12B without a bone aperture.

The connector section 22 connects the first leg section 18 to the second leg section 20. As provided herein, the connector section 22 includes a deformable region 22A that is movable from the first configuration 14A in which the leg sections 12A, 12B are spaced apart a first distance 24 (illustrated in FIG. 1A) and the second configuration 14B in which the leg sections 12A, 12B are spaced apart a second distance 26 (illustrated in FIG. 1C) that is less than the first distance 24.

In certain embodiments, compression of the deformable region 22A causes the deformable region 22A to move from the first configuration 14A to the second configuration 14B. As a result thereof, the bone staple 10 can be easily moved from the first configuration 14A to the second configuration 14B, and the bone regions 12A, 12B are precisely pull together.

The difference between the first distance 24 and the second distance 26 can vary according to the design requirements of the bone staple 10. For example, in alternative, non-exclusive embodiments, the second distance 26 can be approximately 0, 0.5, 1, 2, 3, 4, 5, 6, 7, or 8 millimeters less than the first distance 24. As an example, the first distance 24 can be between approximately 0.5 to 1.5 inches.

Figure 2A:
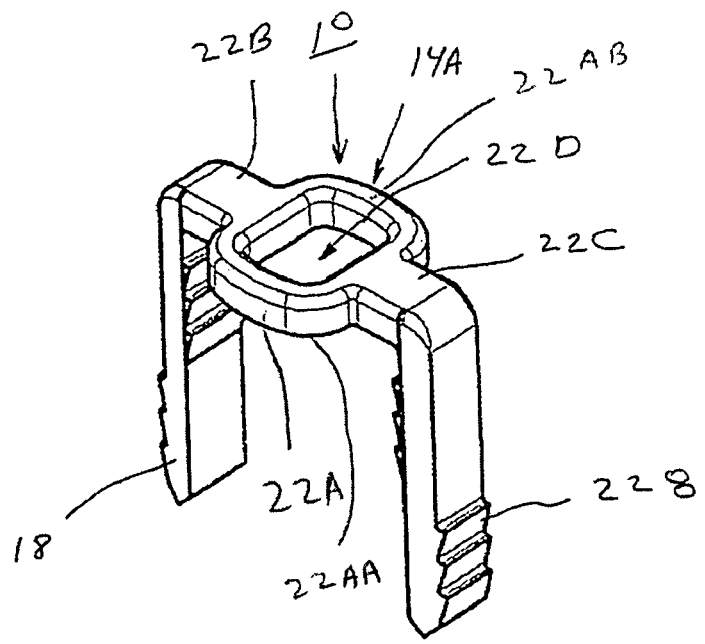
FIG. 2A is a perspective view of a first embodiment of the bone staple in the first configuration.
Figure 2B:
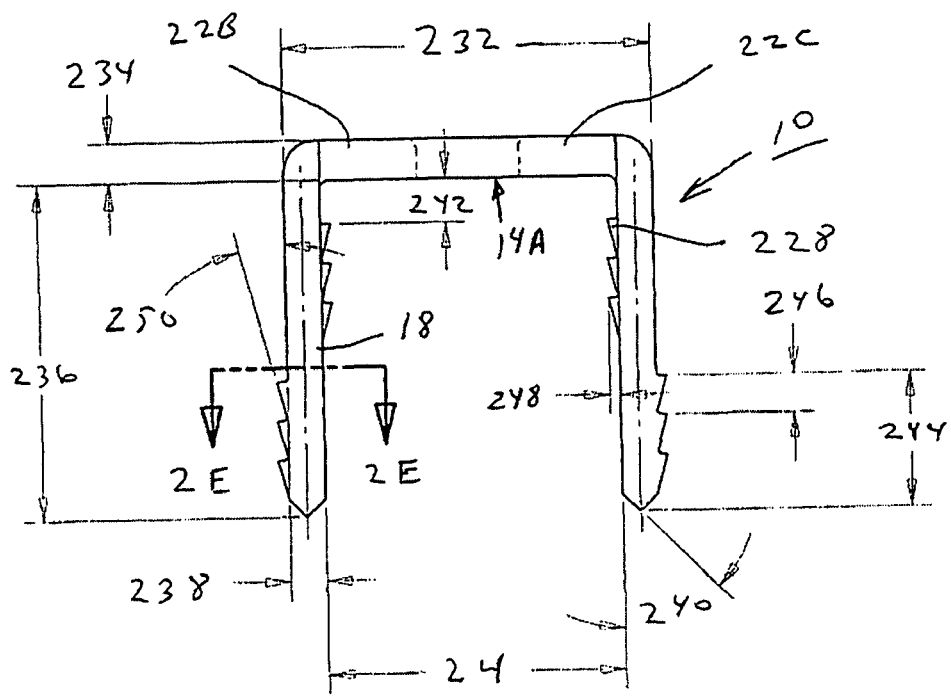
FIG. 2B is a side view of the bone staple of FIG. 2A.

FIG. 2A is a perspective view, FIG. 2B is a side view, FIG. 2C is an end view, FIG. 2D is a top view of the bone staple 10 in the first configuration 14A and FIG. 2E is a cut-away view taken on line 2E-2E in FIG. 2B. The design, size and shape of the bone staple 10 can vary pursuant to the teachings provided herein.

In these Figures, each of the leg sections 18, 20 is generally straight beam shape and has a generally trapezoidal cross-sectional shape. Alternatively, one or both of the leg sections 18, 20 can have another configuration. For example, one or both of the leg sections 18, 20 can have a generally square, round, or oval cross-sectional shape.

Additionally, one or both of the leg sections 18, 20 can include one or more bone engagers 228 that engage the respective bone region 12A, 12B (illustrated in FIGS. 1A-1D) to hold the respective leg section 18, 20 in the bone region 12A, 12B. In FIGS. 2A-2C, each of the leg sections 18, 20 includes three spaced apart bone engagers 228 that face inward, and three spaced apart bone engagers 228 that face outward. In this embodiment, each of the bone engagers 228 is generally wedge shaped and is designed to engage the respective bone region 12A, 12B.

The connector section 22 connects the leg sections 18, 20 and allows the leg sections 16, 18 to move between the configurations 14A, 14B to urge the bone regions 12A, 12B together. As provided above, the connector section 22 includes the deformable region 22A that is compressed to move the leg sections 16, 18 between the configurations 14A, 14B. Additionally, the connector section 22 can include one or more non-deformable regions. For example, in the Figures, the connector section 22 includes a first non-deformable region 22B that secures the deformable region 22A to the first leg section 18, and a spaced apart second non-deformable region 22C that secures the deformable region 22A to the second leg section 20. In this embodiment, each of the non-deformable regions 22B, 22C is generally straight beam shaped. Alternatively, one of both of the non-deformable regions 22B, 22C can have another shape or configuration.

In one embodiment, the deformable region 22A is substantially square ring shaped with rounded/arched corners, and defines a region aperture 22D that is substantially square with rounded/arched corners in the first configuration 14A. Stated in another fashion, the deformable region 22A includes a pair of slightly arched regions 22AA, 22AB that connect the non-deformable regions 22B, 22C together.

Figure 1D:
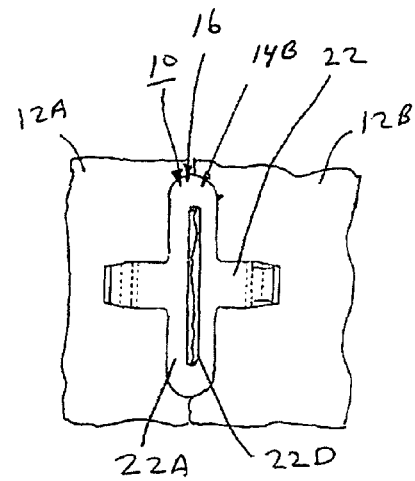
FIG. 1D is a simplified top view of the first bone region, the second bone region, and the bone staple of FIG. 1A in the second configuration.

Further, as illustrated in FIG. 1D, the deformable region 22A is deformed to be substantially oval ring shaped with rounded corners, and the region aperture 22D is substantially oval shaped in the second configuration 14B. Moreover, because of the curved shape of the arched regions 22AA, 22AB, compression of the deformable region 22A results in a controlled buckling of the deformable region 22A in which arched regions 22AA, 22AB are compressed and expanded outward.

Referring back to FIG. 2D, in one embodiment, the deformable region 22A defines an engagement perimeter 22E that is engaged by a compression tool 330 (illustrated in FIG. 3) so that the compression tool 330 can compress the deformable region 22A. In FIG. 2D, the engagement perimeter 22E defines four spaced apart, engagement areas 22F that are engaged with the compression tool 330. In this embodiment, the engagement areas 22F extend transversely to the non-deformable regions 22B, 22C to that they can be engaged by the compression tool 330. For example, the engagement areas 22F can extend substantially perpendicular to the non-deformable regions 22B, 22C.

The size and shape of the various regions of the bone staple 10 can be varied pursuant to the teachings provided herein. Referring to FIGS. 2B-2D, in one non-exclusive embodiment, in the first configuration 14A, (i) the connector section 22 has a length 232 of between approximately 0.567 and 1.236 inches, (ii) the connector section 22 has a thickness 234 of approximately 0.06 inches, (iii) the leg sections 18, have a length 236 of between approximately 0.433 and 0.709 inches, (iv) the leg sections 18, 20 have a thickness 238 of approximately 0.055 inches, (v) the distal tip of each of the leg sections 18, 20 is at an angle 240 of approximately 45 degrees, (vi) the inner bone engagers 228 start a distance 242 of approximately 0.07 inches from the connector section 22C, (vii) the outer bone engagers 228 start a distance 244 of approximately 0.21 inches from the distal tip of the leg sections 18, 20, (viii) each of the bone engagers 228 has a length 246 of approximately 0.06 inches, a maximum thickness 248 of approximately 0.016 inches, and an angled face 250 of approximately 15 degrees, (ix) the deformable region 22A has a wall thickness 252 of approximately 0.055 inches, (x) the region aperture 22D has a width 254 of approximately 0.205 inches and a length 256 of approximately 0.157, and (xi) the leg sections 18, 20 have a width 258 of between approximately 0.120 inches. Alternatively, the bone staple 10 can have dimensions that are different than the example described above.

FIG. 3 is a side view of the bone staple 10 and the compression tool 330 used to compress the deformable region 22A of the bone staple 10. The design of the compression tool 330 can vary. In FIG. 3, the compression tool 330 includes a tool grip 360 that engages the engagement perimeter 22E of the deformable region 22A, a first handle 362 and a second handle 364 that pivots relative to the first handle 362 to move the tool grip 360 and compress the deformable region 22A. In the embodiment illustrated in FIG. 3, the tool grip 360 includes a pair of space apart first projections 366 (only one is shown in FIG. 3) that move with and that are secured to the first handle 362, and a pair of spaced second projections 368 (only one is shown in FIG. 3) that move with the second handle 364. The first projections 366 engage the engagement perimeter 22E on opposite sides of the first non-deformable region 22B (illustrated in FIG. 2D), and the second projections 368 engage the engagement perimeter 22E on opposite sides of the second non-deformable region 22C (illustrated in FIG. 2D). Further, the first projections 366 and the second projections 368 engage the engagement perimeter 22E on opposite sides of the region aperture 22D (illustrated in FIG. 2D).

With this design, movement of the second handle 364 relative to the first handle 362 causes the second projections 368 to move towards the first projections 366 and to compress the deformable region 22A.

Figure 4A:
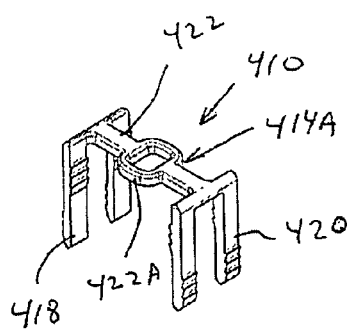
FIG. 4A is a perspective view of a second embodiment of the bone staple in the first configuration.
Figure 4B:
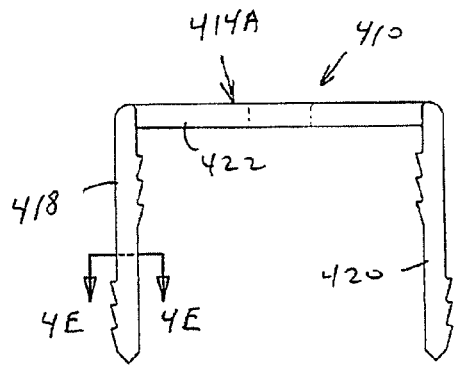
FIG. 4B is a side view of the bone staple of FIG. 4A.
Figure 4C:
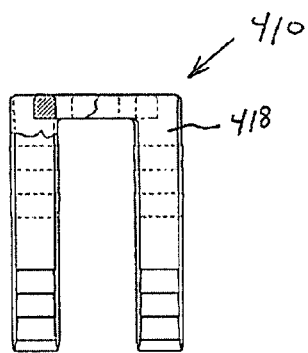
FIG. 4C is an end view of the bone staple of FIG. 4A.
Figure 4D:
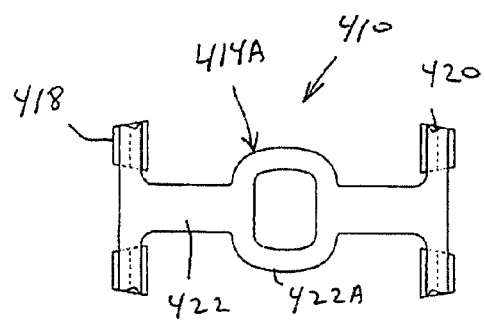
FIG. 4D is a top view of the bone staple of FIG. 4A.
Figure 4E:
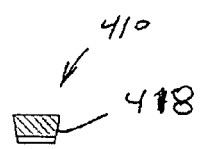
FIG. 4E is a cut-away view taken on line 4E-4E in FIG. 4A

FIG. 4A is a perspective view, FIG. 4B is a side view, FIG. 4C is an end view, FIG. 4D is a top view of another embodiment of a bone staple 410 in the first configuration 414A and FIG. 4E is a cut-away view taken on line 4E-4E in FIG. 4A. The design of this bone staple 410 is somewhat similar to the bone staple 10 described above and illustrated in FIGS. 2A-2E. However, in this embodiment, the bone staple 410 includes two, spaced apart first leg sections 418 that are inserted into the first bone region 12A (illustrated in FIGS. 1A-1D), and two, spaced apart second leg sections 420 that are inserted into the second bone region 12B (illustrated in FIGS. 1A-1D). Further, the connector section 422 connects the first leg sections 418 to the second leg sections 420. Moreover, the connector section 422 includes a deformable region 422A that is similar to the deformable region 22A described above.

In certain embodiments, because of the doubling up of the leg sections 418, 420, the bone staple 410 is able to better secure the bone regions 12A, 12B.

It should be noted that the bone staple 410 could be designed with more than two first leg sections 418 and/or more than two second leg sections 420, or that the number of first leg sections 418 can be different than the number of second leg sections 420.

Figure 5A:
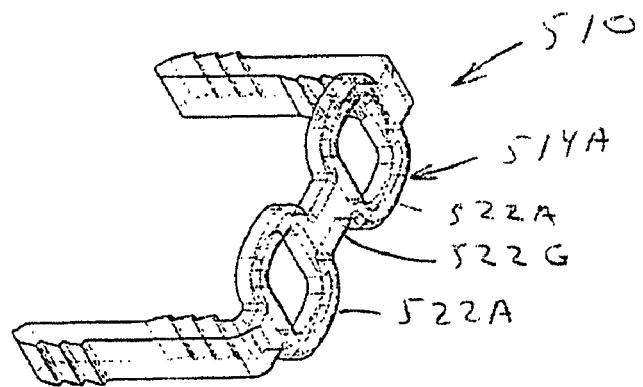
FIG. 5A is a perspective view of a third embodiment of the bone staple in the first configuration.
Figure 5B:
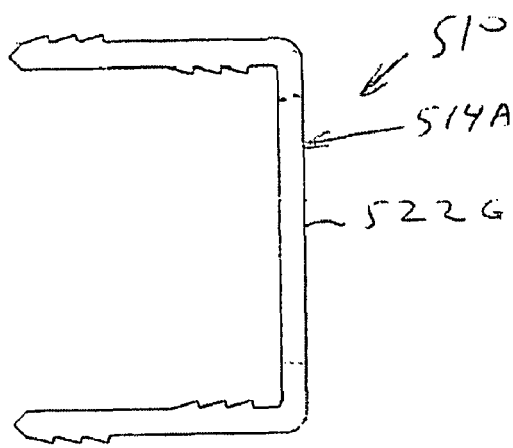
FIG. 5B is a side view of the bone staple of FIG. 5A.
Figure 5C:
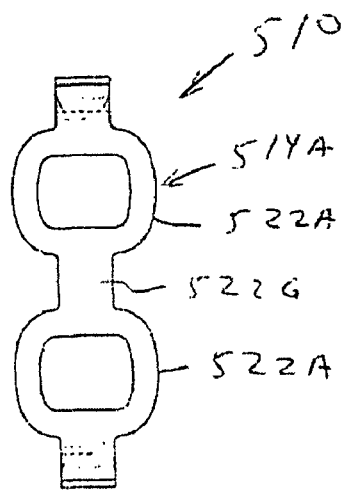
FIG. 5C is a top view of the bone staple of FIG. 5A.

FIG. 5A is a perspective view, FIG. 5B is a side view, and FIG. 5C is a top view of another embodiment of a bone staple 510 in the first configuration 514A. The design of this bone staple 510 is somewhat similar to the bone staple 10 described above and illustrated in FIGS. 2A-2E. However, in this embodiment, the bone staple 510 includes two, spaced apart deformable regions 522A that are separated by a non-deformable region 522G and are act in series. With this design, each of the deformable regions 522A can be independently deformed. This design provides a larger range of possible movement to pull the bone regions 12A, 12B together. For example, one or both of the deformable regions 522A can be partially or fully compressed as needed to achieve the desired amount of movement to pull the bone regions 12A, 12B together.

While the particular bone staple 10, 410, 510 as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A bone staple for securing a first bone region to a second bone region, the bone staple comprising:
a staple body including (i) a first leg section that is insertable into the first bone region, (ii) a second leg section that is insertable into the second bone region, and (iii) a connector section that connects the first leg section to the second leg section, the connector section including a deformable region that is movable from a first configuration in which the first and second leg sections are spaced apart a first distance and a second configuration in which the first and second leg sections are spaced apart a second distance that is less than the first distance, wherein the deformable region includes a pair of spaced apart arched regions, wherein compression of the deformable region causes the deformable region to move from the first configuration to the second configuration and the arched regions to compress and move outward;
wherein the connector section includes a first non-deformable region and a spaced apart second non-deformable region.

2. The bone staple of claim 1 wherein the deformable region is substantially square ring shaped in the first configuration.

3. The bone staple of claim 2 wherein the deformable region defines a region aperture that is substantially square in the first configuration.

4. The bone staple of claim 3 wherein the deformable region is substantially oval shaped in the second configuration.

5. The bone staple of claim 4 wherein the region aperture is generally rectangular shaped in the second configuration.

6. The bone staple of claim 1 wherein the staple body includes another first leg section that is insertable into the first bone region and another second leg section that is insertable into the second bone region.

7. A bone staple for securing a first bone region to a second bone region, the bone staple comprising:
a staple body including (i) a first leg section that is insertable into the first bone region, (ii) a second leg section that is insertable into the second bone region, and (iii) a connector section that connects the first leg section to the second leg section, the connector section including a first deformable region that is movable from a first configuration in which the first and second leg sections are spaced apart a first distance and a second configuration in which the first and second leg sections are spaced apart a second distance that is less than the first distance, wherein the first deformable region includes a pair of spaced apart arched regions, wherein compression of the first deformable region causes the first deformable region to move from the first configuration to the second configuration and the arched regions to compress and move outward;
wherein the connector section includes a second deformable region that is movable from a third configuration in which the first and second leg sections are spaced apart a third distance and a fourth configuration in which the first and second leg sections are spaced apart a fourth distance that is less than the third distance.

8. A bone staple for securing a first bone region to a second bone region, the bone staple comprising:
a staple body including (i) a first leg section that is insertable into the first bone region, (ii) a second leg section that is insertable into the second bone region, and (iii) a connector section that connects the first leg section to the second leg section, the connector section including a deformable region that is movable from a first configuration in which the first and second leg sections are spaced apart a first distance and a second configuration in which the first and second leg sections are spaced apart a second distance that is less than the first distance, wherein the deformable region is substantially square ring shaped in the first configuration and the deformable region includes a pair of spaced apart arched regions so that compression of the deformable region causes the arched regions to compress and move outward with respect to the first and second leg sections;
wherein the connector section includes a first non-deformable region and a spaced apart second non-deformable region.

9. The bone staple of claim 8 wherein the deformable region defines a region aperture that is substantially square in the first configuration.

10. The bone staple of claim 9 wherein the deformable region is substantially oval ring shaped in the second configuration.

11. The bone staple of claim 10 wherein the region aperture is generally rectangular shaped in the second configuration.

12. The bone staple of claim 8 wherein the staple body includes another first leg section that is insertable into the first bone region and another second leg section that is insertable into the second bone region.

13. A method for securing a first bone region to a second bone region, the method comprising:
   providing a staple body including (i) a first leg section, (ii) a second leg section, and (iii) a connector section that connects the first leg section to the second leg section, the connector section including a deformable region that has spaced apart arched regions and is movable from a first configuration in which the first and second leg sections are spaced apart a first distance and a second configuration in which the first and second leg sections are spaced apart a second distance that is less than the first distance;
   inserting the first leg section into the first bone region;
   inserting the second leg section into the second bone region; and
   compressing the deformable region to move the deformable region from the first configuration to the second configuration and to move the arched regions outwardly;
   wherein the connector section has a first non-deformable region and a spaced apart second non-deformable region.

14. The method of claim 13 wherein the deformable region is substantially square ring shaped and defines a region aperture that is substantially square in the first configuration.

15. The method of claim 14 wherein the deformable region is substantially oval ring shaped and the region aperture is generally rectangular shaped in the second configuration.

16. The method of claim 13 wherein the staple body includes a pair of spaced apart first leg sections that extend into the first bone region and a pair of spaced apart second leg sections that extend into the second bone region.

* * * * *